US007890285B2

(12) United States Patent  (10) Patent No.: US 7,890,285 B2
Manfredi  (45) Date of Patent: *Feb. 15, 2011

(54) SCALABLE INTEGRATED TOOL FOR COMPLIANCE TESTING

(75) Inventor: Charles Manfredi, Oakhurst, NJ (US)

(73) Assignee: Agilent Technologies, Inc., Santa Clara, CA (US)

( * ) Notice: Subject to any disclaimer, the term of this patent is extended or adjusted under 35 U.S.C. 154(b) by 349 days.

This patent is subject to a terminal disclaimer.

(21) Appl. No.: 11/286,198

(22) Filed: Nov. 22, 2005

(65) Prior Publication Data

US 2006/0247885 A1  Nov. 2, 2006

Related U.S. Application Data

(63) Continuation-in-part of application No. 11/119,255, filed on Apr. 29, 2005, now Pat. No. 7,440,863.

(51) Int. Cl.
G01R 31/00 (2006.01)
G06F 11/30 (2006.01)
G21C 17/00 (2006.01)

(52) U.S. Cl. ...................... 702/120; 702/182

(58) Field of Classification Search ............... 702/108, 702/182, 189, 120, 81, 115, 117, 118; 703/21, 703/22
See application file for complete search history.

(56) References Cited

U.S. PATENT DOCUMENTS

| 5,280,617 A * | 1/1994 | Brender et al. ............ 717/159 |
| 5,841,771 A * | 11/1998 | Irwin et al. ............... 370/360 |
| 5,878,383 A * | 3/1999 | Carter ...................... 702/182 |
| 5,961,448 A * | 10/1999 | Swenson et al. ............ 600/301 |
| 6,054,865 A * | 4/2000 | Bald et al. ................. 324/551 |
| 6,456,955 B1 | 9/2002 | Andrews et al. |
| 6,876,941 B2 * | 4/2005 | Nightingale .............. 702/120 |
| 6,978,218 B1 | 12/2005 | Kolb et al. |
| 7,440,863 B2 * | 10/2008 | Manfredi .................. 702/108 |
| 2002/0156757 A1 * | 10/2002 | Brown ....................... 707/1 |
| 2002/0183956 A1 * | 12/2002 | Nightingale .............. 702/120 |
| 2002/0192624 A1 * | 12/2002 | Darby et al. ............... 434/236 |
| 2003/0008648 A1 | 1/2003 | Bims et al. |
| 2003/0084340 A1 | 5/2003 | Schertz et al. |
| 2004/0109453 A1 | 6/2004 | Wirth |
| 2004/0128646 A1 | 7/2004 | Jindal et al. |
| 2004/0145598 A1 | 7/2004 | Parent et al. |
| 2005/0071720 A1 | 3/2005 | Dattaram et al. |
| 2006/0041840 A1 * | 2/2006 | Blair et al. ................ 715/513 |
| 2006/0077895 A1 | 4/2006 | Wright |
| 2006/0155411 A1 * | 7/2006 | Khoche et al. ............ 700/108 |
| 2006/0161836 A1 * | 7/2006 | Thomson et al. .......... 715/505 |

(Continued)

OTHER PUBLICATIONS

"Standardization of data ow for laboratory automation soft on XML technology", IEEE Xplore, Oct. 2006, 2 pages.

(Continued)

Primary Examiner—Michael P Nghiem

(57) ABSTRACT

Methods, tools, systems and computer readable media for compliance testing instrumentation and/or software. Data from one or more analytical instruments and/or software is inputted, and calculations are performed on the data to produce one or more outputs. At least one of the outputs may be compared to first and second test limits, and compliance status of the at least one output relative to the first and second test limits is reported.

37 Claims, 9 Drawing Sheets

U.S. PATENT DOCUMENTS

| | | | |
|---|---|---|---|
| 2006/0247878 A1* | 11/2006 | Manfredi | 702/108 |
| 2006/0247885 A1 | 11/2006 | Manfredi | |
| 2008/0059123 A1* | 3/2008 | Estberg et al. | 702/188 |
| 2008/0201098 A1* | 8/2008 | Manfredi | 702/108 |
| 2008/0215638 A1* | 9/2008 | Manfredi | 707/203 |

OTHER PUBLICATIONS

"metadata", Webopedia 2007, 2 pages.

Office Action dated Jan. 29, 2010, in U.S. Appl. No. 12/150,030 for "Integrated Tool For Compliance Testing Within An Enterprise Content Management System".

Agilent—Cerity Pharmaceutical for QA/QC. http://www.chem.agilent.com/Scripts/PDS.asp?IPage=272 pp. 2, Mar. 3, 2005.

Waters Laboratory Informatics—Empower TM Chromatography Data Software. http://www.waters.com/watersdivision/contentd.asp?watersit=JDRS-5KXPGA pp. 2, Feb. 18, 2005.

SSI—Chromatography Data System. http://www.scisw.com/products/cds/index2.htm pp. 2, Mar. 3, 2005.

Agilent—Cerity Enterprise Content Manager (ECM) http://www.chem.agilent.com/Scripts/PDS.asp?IPage=16769 pp. 1-2, Feb. 19, 2005.

AnIML—Analytical Information Markup Language. http://animl.sourceforge.net/ pp. 1-8, Feb. 19, 2005.

Microsoft Office Online: Visio 2003 Home Page http://office.microsoft.com/en-us/FX010857981033.aspx pp. 1-2, Apr. 28, 2005.

FormMax—E-Forms Software for Business Forms Designing and Filli . . . http://www.cutepdf.com/Products/FormsMax/ pp. 1-2, Feb. 18, 2005.

Revision of ChemStations Plus—Agilent Technologies http://www.laboratorytalk.com/news/agi//agi134.html pp. 2, Jan. 15, 2002.

* cited by examiner

Instrument Name: [Charlie's Instrument]

Other Name: [　　　　　　　　　　]

11 B O abj<</size 119/ROOT 1 0 R/ID[<B960B8315a5747479ac05a8440ok005e><136c5bfb974a3d4989096ldaO[ ]727a8>]/Length 11/Filter/FlateDecode/DecodeParms<</Columns 4/Predictor 12>>/w[130]Type/XRef/INfor 3 0 R/Index[118]>>stream
xobodzid:o A olo..
endstrean1endobj01 0 ab1cc/Pages 2 O R/Type/Catalog/Names BB O R/AcroFarmcc/Fields[17 O R]/DRcc/Font<c/Helv 47 D R/ZaDb
L15 0 R/Myriac[PFD-Regular 50 D R/Myriac 0 TT D g >/XFA[(xdp:xdp)90 D R(config)92 0 R(tenplac[ ]94 D R(datasets) 96 D
s(localeSet)98 O R(/xdp:xdp)100 D R]>>/StructTreeRoot B D R/Metadata 117 C R/MarkIrrfocc/Marked true>>Dendabj13 0
obj<</MOdDate(0:20041D15151651-04'00')/creationDate(D:20041D15151544-04'00')/creator(Adobe Designer 6.0)/producer(Adobe
Designer 0.0)lendogi049 0 objcc/F4/Type/Annot/Parent 58 D R/Rect[211.352005 427/323029 Z97KIB5D2B
137.414032]/FT/TX/subtype/Midget/P 9 0 R/T(by[ Instrument_Name 10][0/v9Charlie's Instrument)/] AF4<T0 116 0
R>>/StructParett 1/Q D/DAT/NyriadPro-Regular 10.00 TU/Text
Field)/MK<<>>/TTA(form1(0). fsubform[0]. Instrument_name[D])>>openobja114 O]obj nulloendabja115 0
obj>>/Type/Font/Name/ZaDb/BaseFont/ZaptDingbat s/Subtype/Type1>>Dendabj0118[0 obj<</Length 11B/Type/xObject/BBox[0. 0 0. 0
85.833023 10.091003]/Resources<</Font<</MyriadPro-Regular 50 0 R>>/procset[/PDF/text]>>/subtype/FDRM/FORMTYPE 1/Matrix[1.0
0.D 0.0 1.0 0.0 0.0]>>stream
MTX DMC0qul 1 83.833 8.0B1 reownoBT 0/MyriaD]PFD-Regular 10 Tfu2 1.8905 TOD11.31 TLO(charlie's instrument) TjOETOQ1EWCD

SCALABLE INTEGRATED TOOL FOR COMPLIANCE TESTING

CROSS-REFERENCE

This application is a continuation-in-part application of application Ser. No. 11/119,255 filed Apr. 29, 2005, now U.S. Pat. No. 7,440,863, which is incorporated herein by reference in its entirety and to which application we claim priority under 35 USC §120.

BACKGROUND OF THE INVENTION

Qualification of instruments for regulated markets has traditionally followed one of two models: paper-based protocols that are run on instruments using the native controllers of the respective instruments; and external calculations or qualification routines that are embedded into the controlling softwares of the instruments, respectively. Some efforts at automated data collection have required that an alternative data path be employed for the data collection while still controlling the instrument using its native controller. Examples of proprietary embedded software suites include Cerity NDS (Agilent Technologies, Inc. for chemical/pharmaceutical quality assurance and quality control, and Empower CDS (based on Waters Millenium software, Waters, Inc. These software suites are limited to the suite of instruments that they can control.

Thus, even though these suites are proficient for producing data and results for qualification/quality assurance tasks for the particular instruments that they control, such suites cannot provide standardization of the data types that are processed, nor calculations across controller platforms. Further, data is maintained in a proprietary format that requires the collecting data system to be present and functioning for viewing and reprocessing any data used/outputted by these systems.

Recently, an integrated single source of data collection and storage, EZChrom Elite, was introduced by Scientific Software Inc. While offering a relatively large driver set, this solution is still limited by the available drivers that are provided with the solution Further, all of the current solutions, including those mentioned above, as applied to instrument qualification, require decoupling of the native system that controls the instrument to be qualified, in one fashion or another.

It would be desirable to provide a solution capable of incorporating data from different instruments, as well as from different manufacturers, to compile reports thereon. It would be further desirable that such a solution provides standardization among various data types so that one platform can be readily used to generate reports using data generated from instruments having different platforms, and/or still other instruments that aren't included with any established platforms. Accordingly, there is a need for solutions that are generally applicable for use with data generated/collected by instruments from most, if not all manufacturers, to readily prepare reports therefrom and/or otherwise manipulate the data as needed

SUMMARY OF THE INVENTION

Methods, systems and computer readable media for compliance testing at least one of instrumentation and software are provided for: inputting data from at least one analytical instrument or software performing one or more calculations on the data to produce one or more outputs; and selecting from the one or more outputs to populate a final report; wherein the one or more outputs are standardized and are directly comparable to outputs resultant from carrying out the method carried on another set of one or more other analytical instruments, irrespective of manufacturer or model of the other analytical instruments.

Methods, systems and computer readable media may compare at least one of the outputs to first and second test limits, and report compliance status of the at least one output relative to the first test limit and to the second test limit.

Methods, systems and computer readable media are provided for compliance testing at least one of instrumentation and software, by inputting data from at least one analytical instrument or software; performing one or more calculations on the inputted data to produce one or more outputs; comparing at least one of the outputs to first and second test limits; and reporting compliance status of the at least one output relative to the first test limit and to the second test limit.

Methods, systems and computer readable media are provided for compliance testing at least one of instrumentation and software, to display a test protocol form on a user interface and prompt a user to input information regarding a test for qualifying a result of a test; prompt at least one instrument or software associated with an instrument to initiate the test protocol in response to an input by the user into the test protocol displayed on the user interface, or results from another instrument in response to a test protocol run on the another instrument; automatically calculate results of the test protocol run on the at least one instrument; and output status of the results as determined by at least one set of dual test limits.

A system for standardizing characterizations of at least one of analytical hardware and controlling software during compliance testing is provided to include: a data reduction engine configured to reduce outputted by an analytical or other instrument; a calculation engine configured to perform at least one calculation on at least one of the data outputted by an analytical or other instrument and the reduced data to produce one or more outputs required for a set of predefined criteria; and interactive forms providing procedural information including calculation instructions.

These and other advantages and features of the invention will become apparent to those persons skilled in the art upon reading the details of the methods, systems and computer readable media as more fully described below.

BRIEF DESCRIPTION OF THE DRAWINGS

FIG. 5 illustrates an extraction of information from a form.

DETAILED DESCRIPTION OF THE INVENTION

Figure 1:
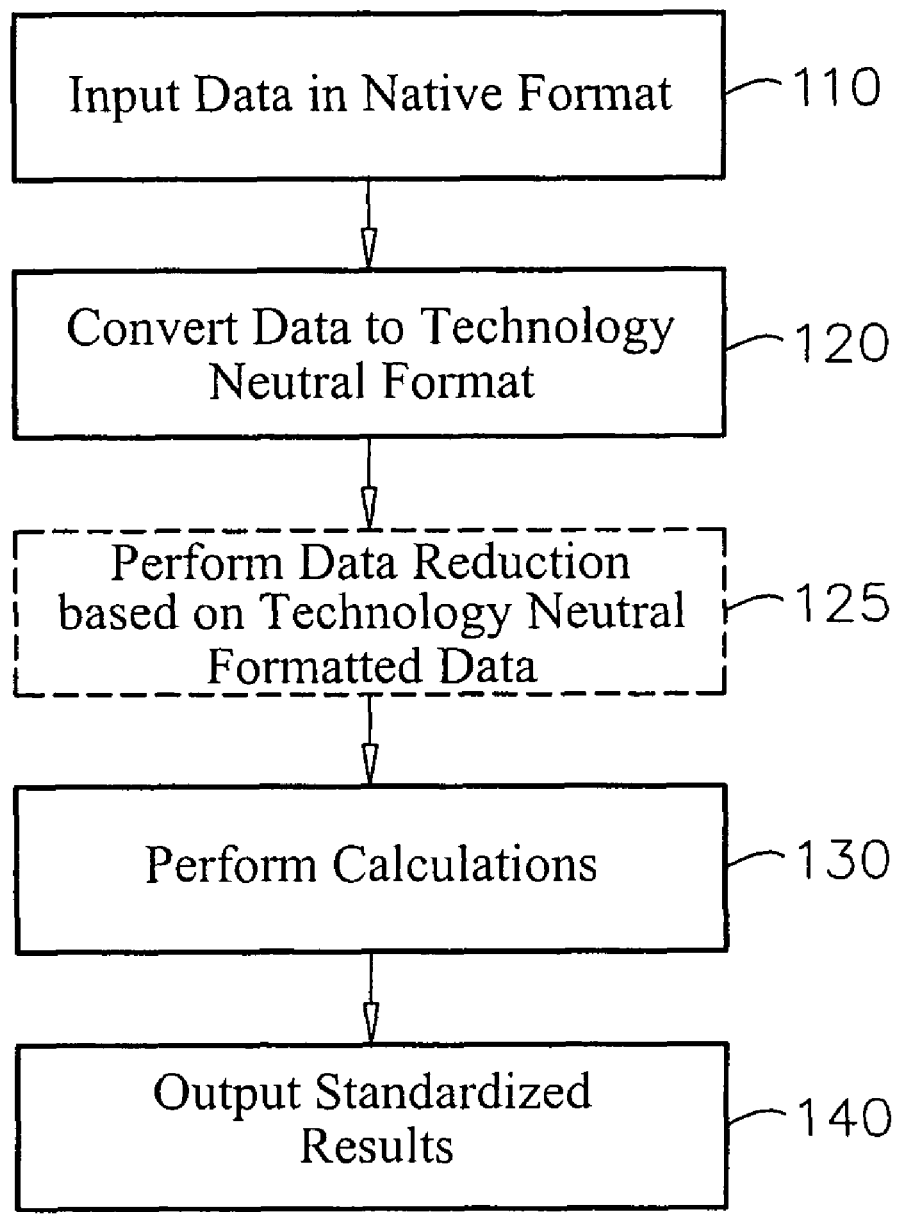
FIG. 1 shows a flowchart of events that may be carried out during processing according to at least one embodiment of the present invention.

Before the present systems, methods and computer readable media are described, it is to be understood that this invention is not limited to particular hardware, software, formats or media described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a limit" includes a plurality of such limits and reference to "the form" includes reference to one or more forms and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

A "platform" as used herein refers to a support infrastructure for acceptance and coordination of tools and applications required to perform a series of related, but diverse tasks.

An "enterprise content manager" refers to a system, scalable to enterprise levels, composed of various hardware and software elements that support the secure collection, indexing and storage of electronic objects.

Disclosed herein are methods, systems and computer readable media for processing data outputted by analytical instruments in a standardized manner so that results of processing are directly comparable with results from processing data outputted by other instruments, regardless of model or manufacturer. Methods, tools and computer readable media for generating, transmitting and storing forms specific for a user's needs are provided, including, but not limited to compliance validation forms. Systems include computers and associated hardware that may be connectable to a network (for internet or intranet use) that can execute rules for a selected form (e.g., one non-limiting example is a form suitable for submission to a regulatory agency such as the FDA). In one embodiment, a system is provided to perform analytical hardware qualifications.

Calculations may be performed to answer a series of questions relating to one or more performance tests designed to determine compliance of an analytical instrument and/or software under consideration with a set of predefined criteria. Such predefined criteria may be criteria defined for regulated industries. For example, "predefined criteria" include, but are not limited to regulations set forth in the Food, Drug, and Cosmetic Act. Predefined criteria are limits and criteria that represent best practices and manufacturers' specifications relating to instrument operation and performance. Compliance to these acceptance criteria provides documented evidence of a device's operation within expectation of intended use. Such compliance is required by law and is listed in the Code of Federal Regulations under headings Part 210, 211, 820, 58, and 21-Part 11 as well as other such regulations and guidance as applies. Optionally, criteria such as limits may be set according to a user's needs, such as when dual limits, are provided, for example.

Forms may be used as built-in records to store data as it occurs, lending to use of the forms for tracking/audit trails. The forms are further useable as a basis for generating reports in a variety of formats. However, as reports are changed, the underlying processes (e.g., the forms containing the data from which the reports are generated) stay the same. Basic universal forms stay the same, while the data they contain can be used to report in many different ways. The forms may be provided to a user in a "wizard-type" environment (i.e., as a "wizard-type" interface), wherein the user is prompted for simple tasks, the response to which are incorporated into a much larger data product. In this way the user only has to deal with simple, single item tasks, one-at-a time.

An enterprise content manager (ECM) may be employed to provide a secure platform to manage all data storage, metadata extraction and archival of data. Alternatively, the system may operate independent of an enterprise content manager to perform data reduction, calculations, and output results, as well as other forms-based functions as described herein. One non-limiting example of an ECM that may be employed is a Cerity ECM, available from Agilent Technologies Inc. Since an ECM is an enterprise system, it also provides scalability to the present system.

Referring to FIG. 1, data is inputted to the system in its native format at event 110, for initial conversion to a technology neutral format (event 120) so that all further processing is with respect to data that is all in the same format, regardless of which instrument was used to originally output the data in its native format. Data conversion may be performed when the system is associated with an ECM content manager, by the ECM content manager. Alternatively, data may be provided to the system that is already in a technology neutral format, as for example, when an instrument owner converts the outputted instrument data to a technology neutral format, and then this converted data is directly inputted to the system. Under this option, the system does not perform events 110 and 120, as the data inputted is already in a technology neutral format.

As another option, if data cannot be submitted to the system in a technology neutral format and an ECM is not employed, the analog data outputted by an instrument may be received by the system and then converted via an A/D converter to a digital signal to be inputted into the system. The digital signal may be provided in a technology neutral format, such as a .cdf format (e.g., AIA, AnDI, etc.) or proprietary formats such as: bxx, pts, raw, .ch or dat, for example. Data reduction may be performed at event 125 by a data reduction engine as described below, if needed. By performing calculations/further processing (event 130) on technology neutral formatted data or digital signals having been converted from the analog output of an instrument, with the present system, calculations are thereby standardized, so that results (event 140) are directly comparable between data produced by various instruments, models and manufacturers. The standardization is made possible by the system's ability to convert data from external sources into a technology neutral format, input of data that is already in a technology neutral format, or read proprietary data, which is then data reduced and calculated by common components. Further, this standardization may be applied to data sources manually, semi-automatically (requiring some manual application) or automatically, and such data may require data reduction, or may be in a ready-to-process form. In this way data that characterizes the operation of instrumentation or controlling data systems can be used for the purposes of qualification of said device irrespective of proprietary or native format. One non-limiting example of a technology neutral format that may be employed by the present system is referred to as Analytical Information Markup Language (AnIML, see http://animl.sourceforge.net/) which is an open source, XML-based standard for formatting analytical data. By converting all data to a technology neutral format, and then processing the converted data all according to the same protocols, results are generated that are standardized and directly comparable among results for different instruments which may be different models and/or made by different manufacturers.

As noted, the computerized data system (CDS) that is in place for operating the instrument(s) to obtain the data on which a report is to be generated may be used as direct input to the system. Thus, original data collected for a report may be accomplished using the native controlling software (of the CDS) of the instrument(s) without the need to go through external analog to digital conversion or other manipulation. As noted, the data collected may alternatively be collected in analog form and A/D converted for input to the system. Original data, which may be preserved for possible reanalysis by the native CDS, may also be converted to an accepted technology-neutral format allowing the data to be submitted to a single reprocess and calculation engine for consistent reduction and processing. By using the native CDS, the present system may also make use of the drivers employed by the native CDS, thereby further facilitating the universal applicability of the present system to different types of instruments and to instruments having different standards/CDS's as a result of being produced by different manufacturers.

Figure 2:
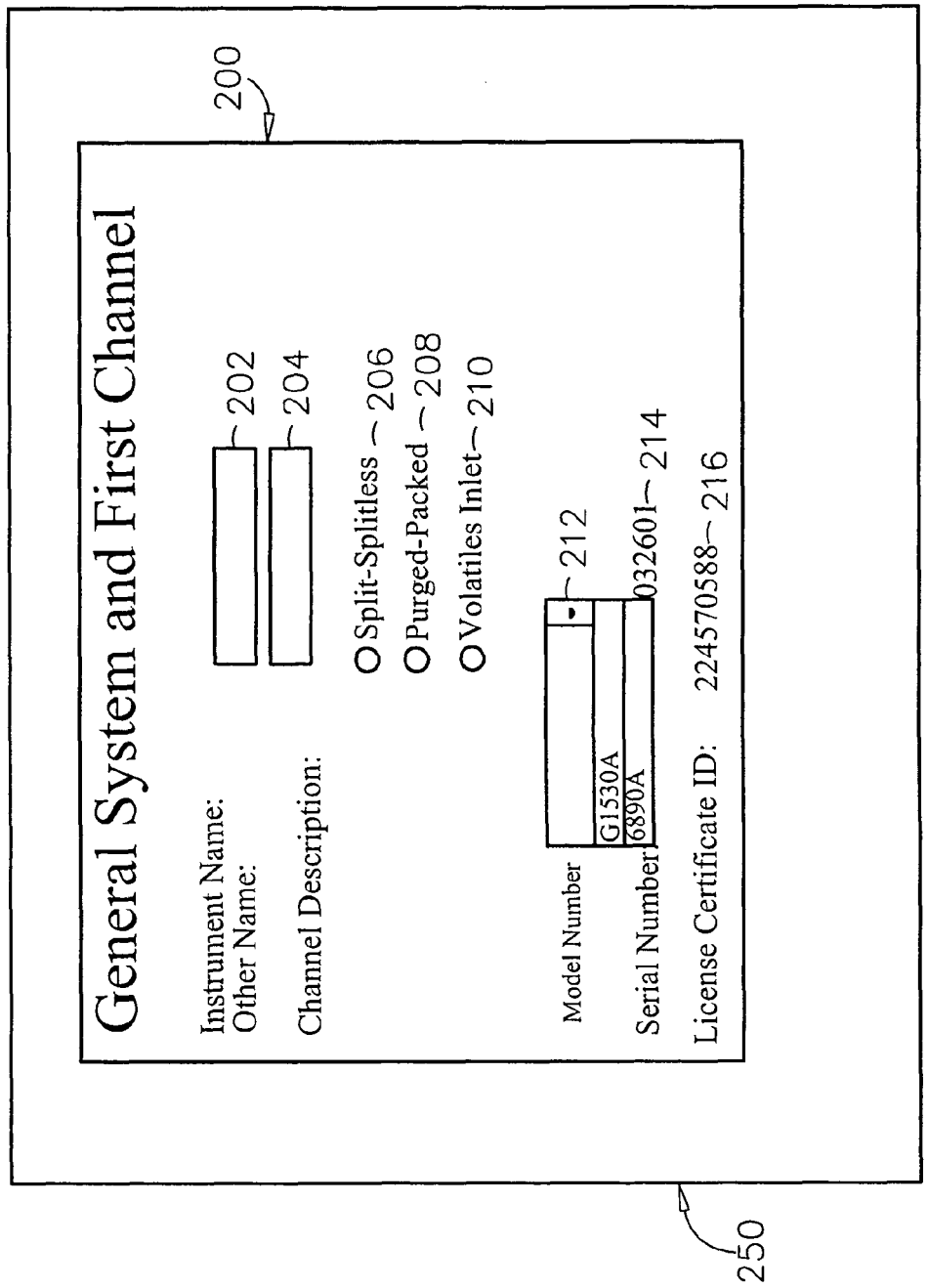
FIG. 2 illustrates one example of a form that may be used by an embodiment of the present invention.

Instructions may be instantiated as forms 200 (e.g., see FIG. 2) to provide procedural information, while also functioning as data repositories. Forms 200 may be constructed in many different ways and presented to have as many different appearances, some of which are dictated by the information to be displayed/stored and much of which may be flexibly designed. The instrument/process type as well as the required input to the form 200 dictates the content and appearance of form 200. FIG. 2 shows one example of a form 200 which is in no way meant to be limiting, as many different forms may be provided by the system. In FIG. 2, form 200 includes fields instructing the following data to be inserted and stored: Instrument Name 202; Other Name 204; Channel Description: Split-Splitless 206, Purged-Packed 208, Volatiles Inlet 210; Model Number 212; Serial Number 214; and License Certificate ID 216. Forms 200 may be run as an applications program interface (API) and, as such need not ever be even visualized by a user of the system when all data fields can be automatically identified from the technology neutral formatted data and/or native CDS and populated into form 200 to complete all data fields.

Alternatively, or additionally, a user interface 250 may be provided to display one or more forms. In a case where automatic population of all required data is not possible, user interface 250 can display form 200 so that a user can interactively select an entry (as in the case of Model Number 212, shown in FIG. 2, where a drop down menu is provided from which the user can select the proper entry) or manually input an entry, such as by typing, cutting and pasting, scanning or some other alternative data entry mechanism that requires intervention on the part of the user. Further alternatively, the user interface 250 may be optionally used to enter all data required by a form, either as a result of user preference to do so, or because an instrument being considered is sufficiently old or unsophisticated, so as to lack a sophisticated enough software interface to supply some or all of the data automatically by interfacing with the present system.

As another alternative, a user interface may display a test protocol that prompts the user to input information regarding results of a test. In some instances, the test may be automated, wherein the system may prompt one or more lab instruments to initiate a test protocol in response to one or more answers inputted into the user interface by the user in response to questions asked on an interactive form/test protocol, or in response to results from another instrument (e.g., in response to a test protocol designed for that instrument).

The system may also provide a report detailing processes and/or instruments that do not comply with selected specifications (i.e., a protocol deviation form).

The forms may be XML based forms that can be directly rendered to a final report (such as in pdf format, or other format suitable for paper documents, for example). Thus, for example, forms 200 may be displayed in pdf or some other document format on user interface 250 when part or all of them are to be interactively filled out by a user. As noted, part or all of forms 200 may be programmatically filled out from auto detection of calculation engines provided by the system. Forms 200 may be left in native XML format and thereby function as storage for the data that they contain. Forms 200 may be further rendered from the XML format to an HTML version for use with a browser.

When used interactively, forms may be presented to a user according to need and thus, forms that apply only to the instrument(s) under test are presented, thereby reducing delivery complexity and error potential, while at the same time providing audit trails for tracking, since the forms may be saved, as noted above. By converting proprietary data into standardized data (i.e., data having a technology neutral format), the system may provide data in a standardized output form. Thus, inconsistent output from instruments can be converted to consistent input to an engine that can do calculations in a very predictable, standardized way, which is an important consideration for qualification and compliance reports.

Figure 3:
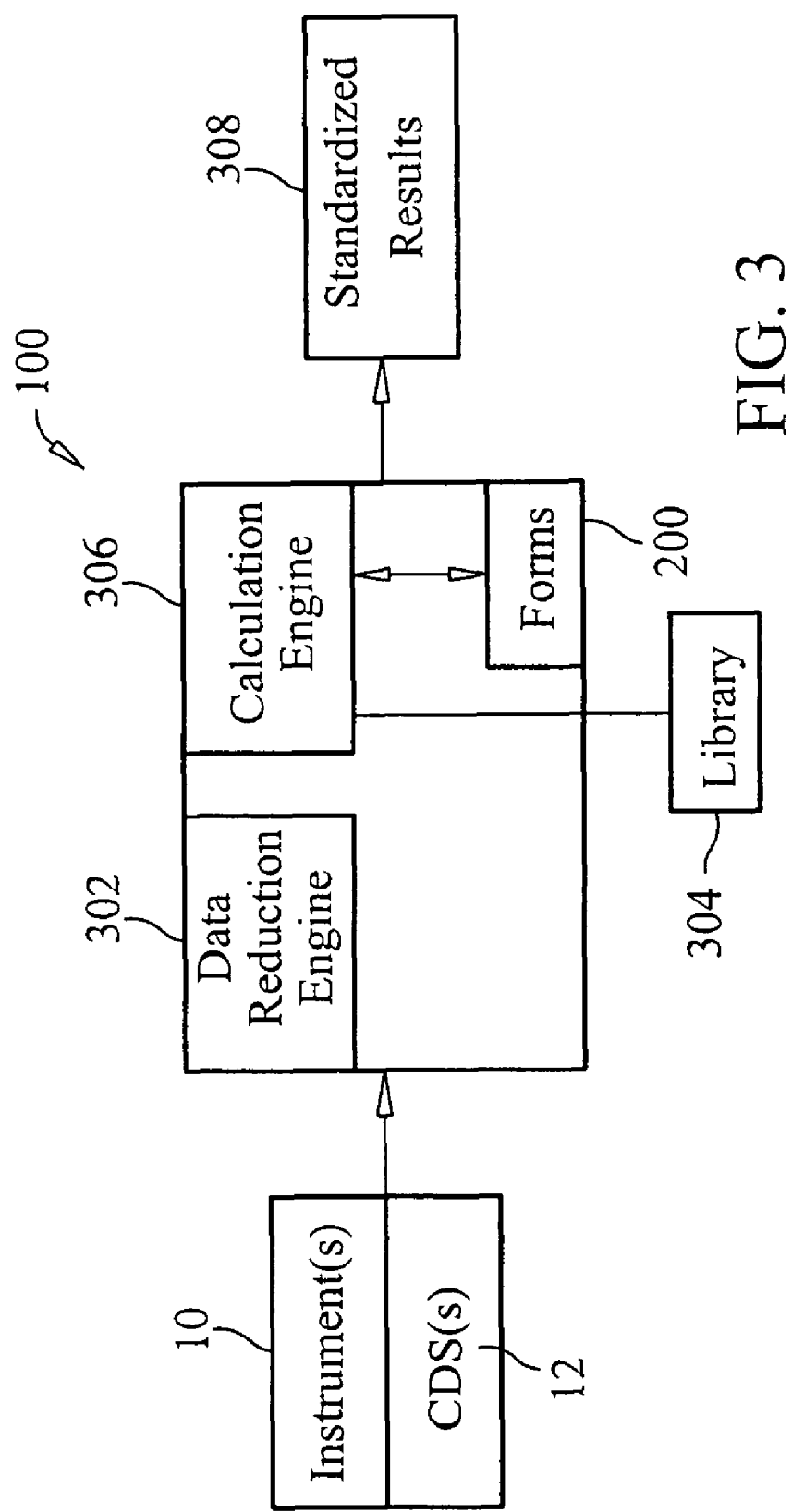
FIG. 3 is a schematic flow chart illustrating process flow according to an embodiment of the present invention.

Once native data has been converted into technology neutrally formatted data, or, alternatively, after converting analog signals outputted from an instrument to digital signals, or after receiving digital output signals from an instrument, metadata may be created by data reduction engine 302 (FIG. 3) of the system 100 so that algorithms from the instrument's 10 system(s) do not need to be relied upon, and this further ensures standardization of results. For example, for application to chromatography, the present system does not rely upon the software 12 running the chromatography instrument 10 from which the raw data is generated to determine what is a peak in the data or where to define the location of that peak, as such determinations are made based upon calculations and algorithms run by the data reduction engine 302 of the present system. Data reduction engine 302 reads the data having been converted into technology neutrally formatted data, or otherwise, and converts this digital representation of an analog function into data representing features described/characterized by the data (e.g., peaks, noise, gradient steps, etc.). The same applies to other calculations, such as those determining and/or filtering noise levels, etc. Using this approach, consistent results are determined for data across the board, whether a particular type of instrument 10 was manufactured by one or another particular manufacturer, or whether the instrument 10 is a different model than another, both of which data is being processed from.

As one example, signal data from a chromatography instrument 612, as inputted to system 100 by the native controlling software for the instrument is just a series of changing signals over time. Reduction engine 302 converts these signals (which may or may not have been converted to a technology neutral format into useable data, e.g., peak area, noise calculations, etc.—which can be fed to calculation engine 306— e.g., there are 5 peaks and those 5 peaks have peak areas of 2, 2.1, 1.9, 2 and 2 and the mean is X, with standard deviation of Y, etc. so that these values can be compared to an acceptance standard, or with like values calculated with regard to another instrument 612.

Depending upon the instrument that has generated the data, a data reduction engine 302 may not even be needed. For example, a balance already outputs data that is reduced to numbers that are useable by calculation engine 306 and so this data does not need to be further reduced, although it may be converted to a technology neutral format. Further, other alternative reduction engines 302 may be included with the system 100 as part of a library that may be accessed for non-standard reduction requirements. By performing data reduction with a component of system 100, this separates reliability on each instrument's software for performing such functions. Accordingly, all data reduction is standardized across reports that are prepared by system 100, and performance is all standardized by evaluation by the same system.

Further, since the data is standardized, only one method need be developed to produce a particular type of report based on the data, as opposed to the current need to create a method for each instrument that employs a different data type or format. Thus, calculation engine 306 can perform calculations based upon a single library 304 (e.g., series of calculations tailored to a specific type of report for a particular type of data reporting). For consistent raw data sets (i.e., technology neutrally formatted data) received by data reduction engine 302, these data sets can be properly manipulated with a single consistent method. Thus although the method for acquisition of data may vary depending upon the computer data system from which the data is being acquired, once that data has been converted to a technology neutral format, the back end processing is consistent (e.g., processing by data reduction and calculation engines, etc.). Library 304 typically contains a set of calculations for performance of the standardized tasks in the back end processing (e.g., calculation/identification of peaks; calculation of statistics describing the data, etc.). With respect to data reduction and calculation, the results may be standardized and independent of the originating data-system or controlled instrument, as noted above. Reports based on those results are fully customizable, as reports ranging from simple summary reports to traditional, fully described compliance protocols may be outputted.

The library can be modified, typically added to, to increase functionality, but it does not have to be a different library based on the data system that the instrument used, contrary to what is currently required. Consequently, calls become consistent and calculations become reusable and portable. For example, a library may be created to calculate peak precision, signal-to-noise, etc., and library 304 may be built to accept only consistent input forms because the input format will always be the same, since the engine for extracting data (data reduction engine 302) will always be the same. Running processes in this way provides consistent metrics across all manufacturers, types and models of instrumentation. For example, peak detection and baseline evaluation can be performed as de facto standards against which all systems/instruments may be evaluated. Thus, such a library 304 is reusable and portable, being applicable to calculation of the defined data specifications based upon data inputted from the data reduction engine 302, and wherein data reduction engine 302 may be applied to data from any applicable instrument for which it makes sense to calculate the prescribed specifications, since the data from the instrument will have been converted to a technology neutral format that the data reduction engine 302 is configured to receive as input.

The standardization of processing will advantageously reduce training requirements for operating personnel, since personnel will no longer need to be trained for operating with regard to each different piece of equipment, but can instead be trained to run the standardized processes. For example, under conditions prior to the present invention, it would not be unusual for an instrument (piece of hardware) 10 to be operating in various locations under multiple (e.g., three) different proprietary operating software platforms. For compliance purposes, it might then be necessary to replicate the compliance procedures as many times as there are multiple platforms. By providing the present system as built on an independent platform, it is not dependent upon the operating software of the particular instrument upon which reports are to be generated. In this way the system is readily adaptable to new/various hardwares as well as softwares, given the generic nature of the protocols.

As noted, system 100 may further employ a calculation engine 306 to perform calculations on the reduced metadata set produced by data reduction engine 302 for formulating standardized results 308. Calculation engine 306 performs calculations on metadata in the reduced metadata set received from data reduction engine 302 as well as any calculations that may need to be performed on other data that has been converted to the technology-neutral format, as instructed by forms 200, such as for the performance of qualification services on analytical instruments as well as other instruments. As noted, forms 200 may act as instructions for processes carried out by calculation engine 306, as well as for data storage repositories of the results of these calculations. Forms 200 can contain any combination of input types including interactive manual input, information detected by software of system 100 and/or the CDS of the instrument being considered and/or calculated reduced data. Forms 200 may further include launch points for executables that perform detection, calculation, or any other function called for by the process. Forms 200 may be version controlled and stored as record of the data collection process leading to a resulting final report.

In this way the stored versions of forms can serve as an audit trail from the time of initial collection of the data all the way through to the time of the issuance of the final report.

When standardizing all data to a technology neutral format and creation of metadata from the same, calculations by calculation engine may be carried out by calls to a consistent and tested library, as the calculations are reusable and portable.

Figure 4:
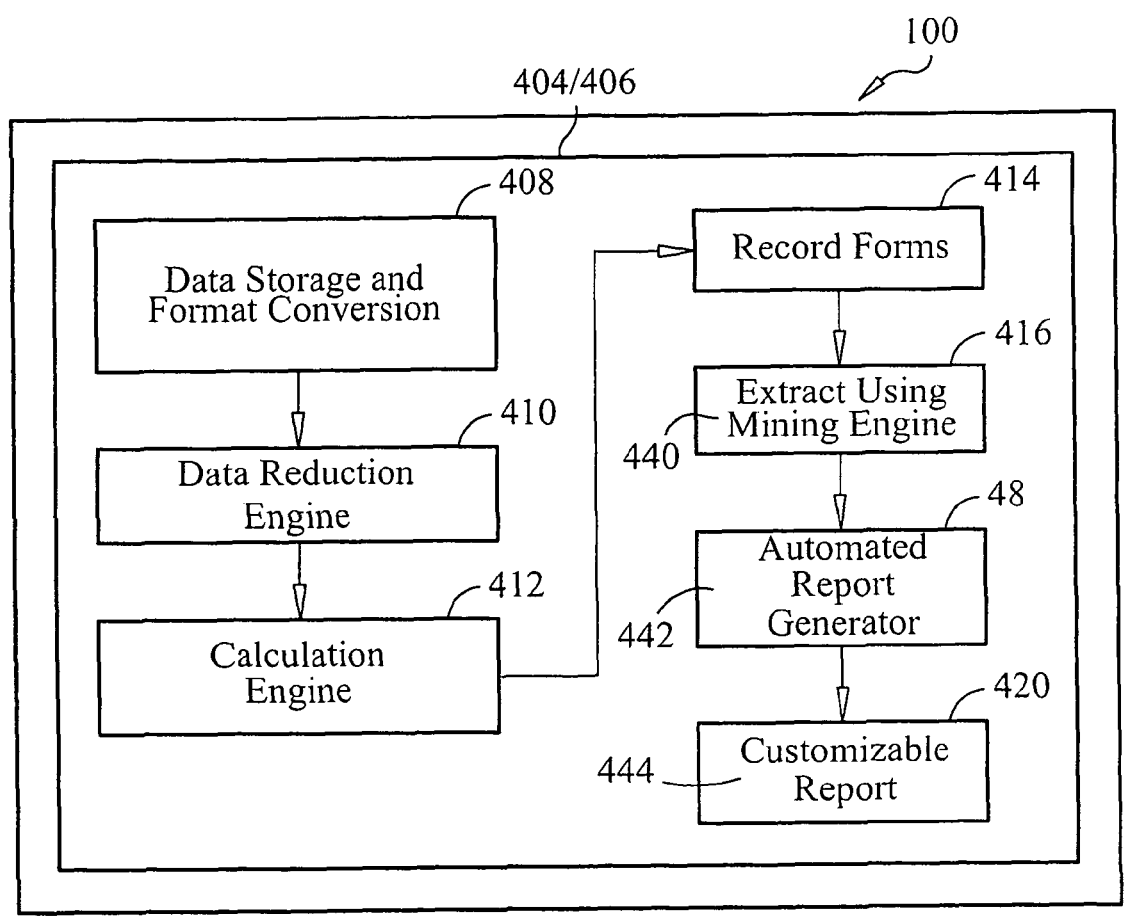
FIG. 4 is a block diagram illustrating functions and processes that may be managed through a business process manager according to an embodiment of the present invention.

In order to manage data storage, metadata extraction and archival of data, as well as compilation of final reports and other form management functions, system 100 may employ an enterprise content manager (ECM) 404, as noted earlier. ECM 404 may provide a secure platform on which to manage the functions described. FIG. 4 illustrates a flowchart of functions and processes that may be managed by ECM 404 via business process manager (BPM) 406. BPM 406 manages flow so that data storage and format conversion (to a technology neutral format) are carried out by ECM 404 at event 408, followed by reprocessing/data reduction by data reduction engine at event 410, functions of which were described above. Further calculations are carried out by calculation engine 306 at event 412, which may be based upon instructions contained in forms 200 and the data populated into form 200 may be recorded and stored in ECM 404 at event 414. The record forms 200 may then be data mined at event 416 by record mining engine 440 to extract specific items of data/metadata that are required to populate a final report.

FIG. 5 illustrates data extraction from a form 200 to obtain information needed for preparing a report, wherein a portion of a record form 200 is shown from which a particular data entry 502 is located. Record mining engine 440 may employ toolsets for mining data, e.g., name-value pairs may be taken from forms 200 and calculation engine 306 may further extract those values needed by identifying such values based upon the names associated with the values in the name-value pairs. Data from a form 200 can be calculated and the resulting calculations may be returned to the same form 200 or to another form 200 as needed for purposes of organization, readability, clarity, etc.

As shown, forms 200 actually do contain the information/data received from the software of the instrument being considered, and that data can be mined to fill out automated report applications or otherwise to fill out a final report 444. In this way, forms 200 act as a repository that can be mined in various ways—compliance, asset management, etc. Once a final report 444 is signed, however, the data that was mined to fill out the final report document 444 can no longer be changed, ensuring inviolable metadata, so that an effective audit trail is maintained.

An automated report application (automated report generator) 442 may be optionally included, and if used, functions to automatically populate documents at event 418 which are then outputted as a customizable report 444 at event 420. Automated report generator 442 is an application that facilitates that construction of configuration-specific documents from a library of all possible configurations. Automated report generator 442 allows documents to be populated with content learned through many various mechanisms, such as the mechanisms that have populated forms 200. An analogy to one function of the automated report application 442 is with reference to an automobile and an automobile user's manual that accompanies the automobile. Because the owner will typically have many options from which to choose from, the owner's manual is typically written to describe each of these options. Thus, for example, if an owner has a particular type of sound system, but there are six different sound system options for the owner's car, in order to access information about the sound system, the owner will typically have to page through descriptions of all six sound systems options in the user's manual until the matching sound system is found. An automated report application for owner's manuals would prepare this user's manual based upon the options chosen by the owner, so that when the owner looked up the description of the sound system, only one sound system would be described in the owner's manual, i.e., the description for the sound system actually selected by the owner for his/her car.

The automatically populated forms 200 as well as the final report 444 may be stored into ECM 404 when an ECM is employed, so that ECM 404 is the location of the initial collection, calculation, meta-data and final data, as well as audit trails. Thus, system 100 may include a relational database with tools such as data reduction engine 302, calculation engine 306, and record mining engine 440, for example, sitting on top of it.

Reports 444 can take on any form, and may be selected by a user. For example, a report may be created in summary form or in full detail, with or without a logo, etc. While the reports 444 are customizable, the underlying forms 200 created by the system 100 do not change so that standardization is preserved. Auto-documentation feature 442 may be optionally provided, as noted above, whereby the user is provided with selectable choices, via user interface 250, to determine the format of the report 444 to be produced. Thus, depending upon the selection made, different groupings of metadata from the underlying forms 200 are selected and combined into a format of the final form selected.

Audit trails may be automatically provided by the metadata stored as forms 200 by ECM 404, as alluded to above. Further BPM 406 may provide e-mail notification, scheduling and review, electronic signature functions, etc.

Figure 6:
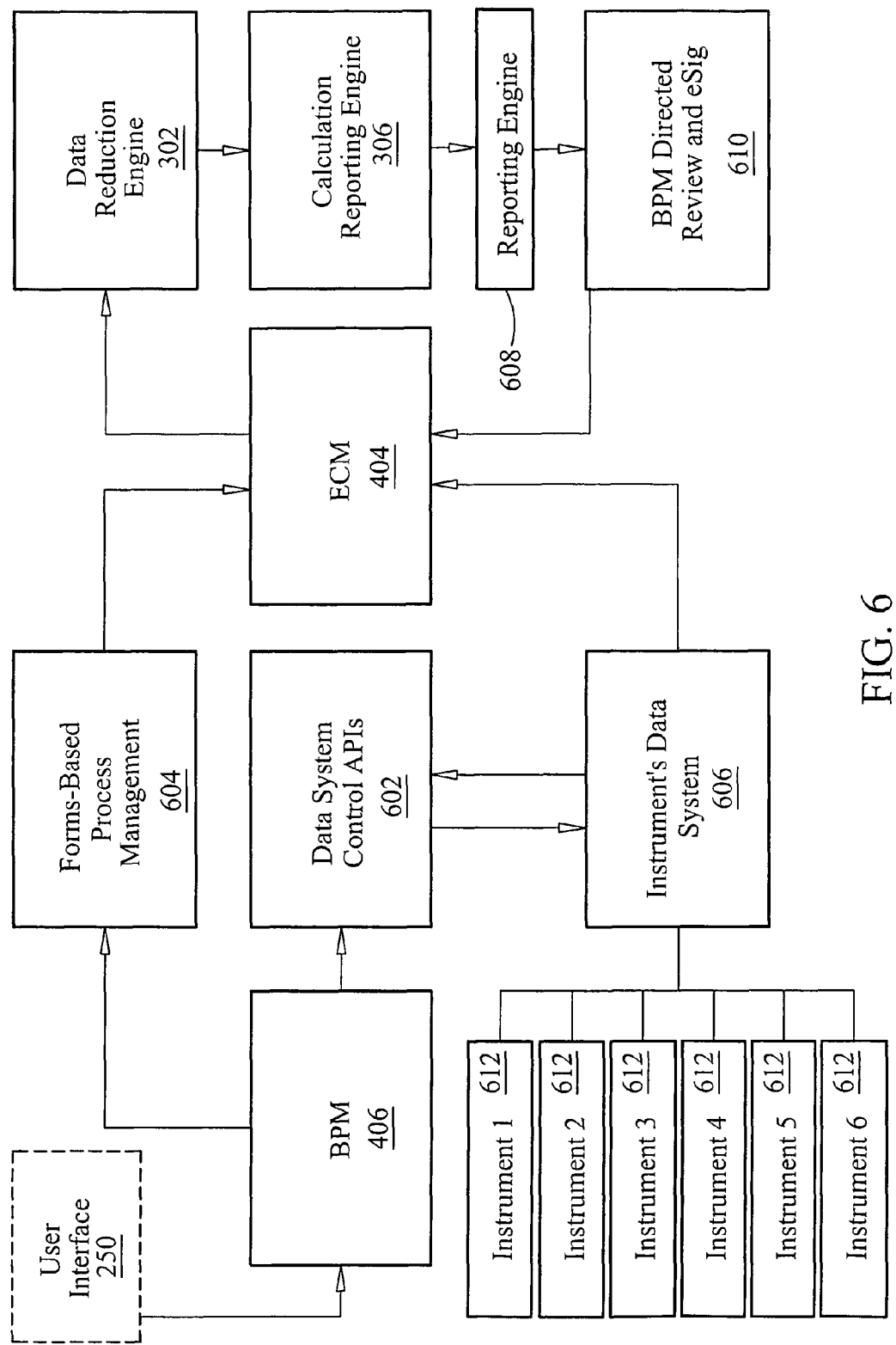
FIG. 6 is a flow chart illustrating further details of process flow by an embodiment of the present invention.

Referring now to FIG. 6, a flow chart that further explains process flow by a system employing an ECM 404 and BPM 406 is shown. As noted above, a user interface may or may not be needed, which may depend upon the choice of the user, the types of instruments being reported upon, and/or whether the system is capable of fully automatically obtaining all information required to generate a final report. System control API's 602 are provided for running processes so that there is not a need to display the process on user interface 250. The business process manager (BPM) 406 permits flexible formatting of process. For example, the process can be changed just by changing/rearranging a flow chart similar to that which is shown in FIG. 6. For example, flow charts used may be flow charts produced by Microsoft Visio e.g., see http://office.microsoft.com/en-us/FX010857981033.aspx, or other alternative chart building software that allows flow charts to be readily modified interactively. Such chart building softwares provide a visual manifestation of a process implemented and controlled by BPM 406. As a simple example, if a current process flow of system 100 includes a process or subprocess defined by steps A>>B>>C>>, but the current user/client requires step C to be performed after step A and before step B, then the current process chart can be interactively rearranged, such as by dragging step C between steps A and B and dropping it there to result in a process/subprocess defined by the steps A>>C>>B. Accordingly, the system 100 provides a great amount of flexibility for customizing the process control, which is then managed by BPM 406 using forms-based process management 604 as was described earlier.

The technology neutral design of system 100 allows any client's or manufacturer's data system (i.e., Instrument's Data System 606) to be fed into ECM 404. Accordingly, any type of instrument, model of instrument or manufacturer of an instrument may be included as instruments 612 from which data can be received by system 100. For example, Instrument 1 may be a liquid chromatography/gas chromatography instrument 612 produced by a first manufacturer, Instrument 2 may be a liquid chromatography/gas chromatography instrument 612 produced by a second manufacturer, Instrument 3 may be still another liquid chromatography/gas chromatography instrument 612 produced by a third manufacturer, Instrument 4 may be a mixed vendor system, Instrument 5 may be a refrigerator with an embedded microprocessor or other associated hardware/software configured to input data to system 100 (or alternatively, data from this instrument may be manually inputted via interface 250 if Instrument 5 is not sufficiently automated), and Instrument 6 may be a centrifuge, wherein the same considerations apply as described with regard to Instrument 5. A "mixed vendor system" refers to systems produced by more than one manufacturer/vendor. Examples of mixed vendor systems include, but are not limited to: a computer data system manufactured by a first vendor and controlling an instrument manufactured by a second vendor; a computer data system produced by a first vendor that controls instruments produced by second, third and fourth different vendors; or a computer data system produced by a first vendor and controlling a single instrument made up of components produced by different vendors, etc. As long as the associated computer data system can successfully drive the mixed vendor system, the present system can process the data in a manner as described.

As noted above, if the instrument's data is proprietary data, the proprietary data may be converted to technology neutral formatted data, (e.g., AnIML, etc.) using data system control API's 602 (or, if provided in human readable form, the data may be added to the forms manually and included into qualification processing with any required calculations, or may be converted from an analog signal outputted by the instrument to a digital signal inputted to the system) and both the proprietary data and the converted (technology neutral, A/D converted, and/or manually inputted) data may be saved in ECM 404.

The data can then be further processed by data reduction engine 302, calculation engine 306 and reporting engine 608. Reporting engine 608 requires at least one of a data mining application (e.g., record mining engine 440) or a middleware component configured to provide an input file to reporting engine 608 to correctly populate a report.

Once final report 444 has been generated, BPM 406 can direct reviews and signatures electronically at event 610. The final report, both signed and unsigned may be stored in ECM 404. Further, all intermediate forms 200 and the data that they store may be stored in ECM 404 to maintain a complete audit trail, as was also discussed. All processing represented in FIG. 6 may be based on forms and the instructions contained therein. WYSIWYG ("what you see is what you get") authoring capability may be provided by the forms designer application for designing forms 200. Secure data handling is ensured by ECM 404. Standardized results are the end product of these methods, providing a clear differentiator over anything that is currently available in the market.

The data path that the instrument 612 uses is the same data path that system 100 uses for reports such as compliance. However, the calculations performed on the data for whatever report is to be produced, do not need to be performed on the instrument itself, nor does the instrument's software need to be employed for performing calculations. Advantageously system 100 provides everything that is needed for performing such calculations. This effectively reduces the native computer data system (CDS) to a controller and data acquirer. Such reduction provides checks on the interplay between the hardware and software of a system to be qualified at each qualification event without burdening the hardware qualification event with data reduction evaluation of the native CDS. This assures that the more frequent requirements for hardware qualification provide the maximum value with respect to CDS verification, without forcing extensive CDS evaluation. Further, the controlling system (CDS) need not be qualified for use in the qualifying of hardware, since it is not used for such purpose by system 100. Rather, system 100 performs calculations on the raw data produced by the instrument (after conversion to a technology neutral format, if necessary), thereby taking the instrument's controlling software out of the loop and effectively separating the instrument's hardware, from the associated software, so that the report can focus on the hardware, independent of qualifying the instrument's controlling software.

The modularity provided by system 100 facilitates modular instrument qualification after repair. The process flow manager 406 may present forms specific to the tests associated with the requalification of a module. The resultant data can be associated with the module, stack and existing compliance documentation to requalify the module. Thus, if a module needs to be repaired, then that module can be requalified, rather than having to requalify the entire system, i.e., qualification may be done on a modular basis.

BPM 406 may control the workflow from collection of data through approvals/signatures of final report 444, and may be tightly integrated into ECM 404. The entirety of processing may be web browser-based or terminal servers-based so that no footprint is imposed upon the user's qualified computer. In instances where ECM 404 has been incorporated into a customer's system, local interfaces (e.g., user interface 250) may be employed.

Figure 7:
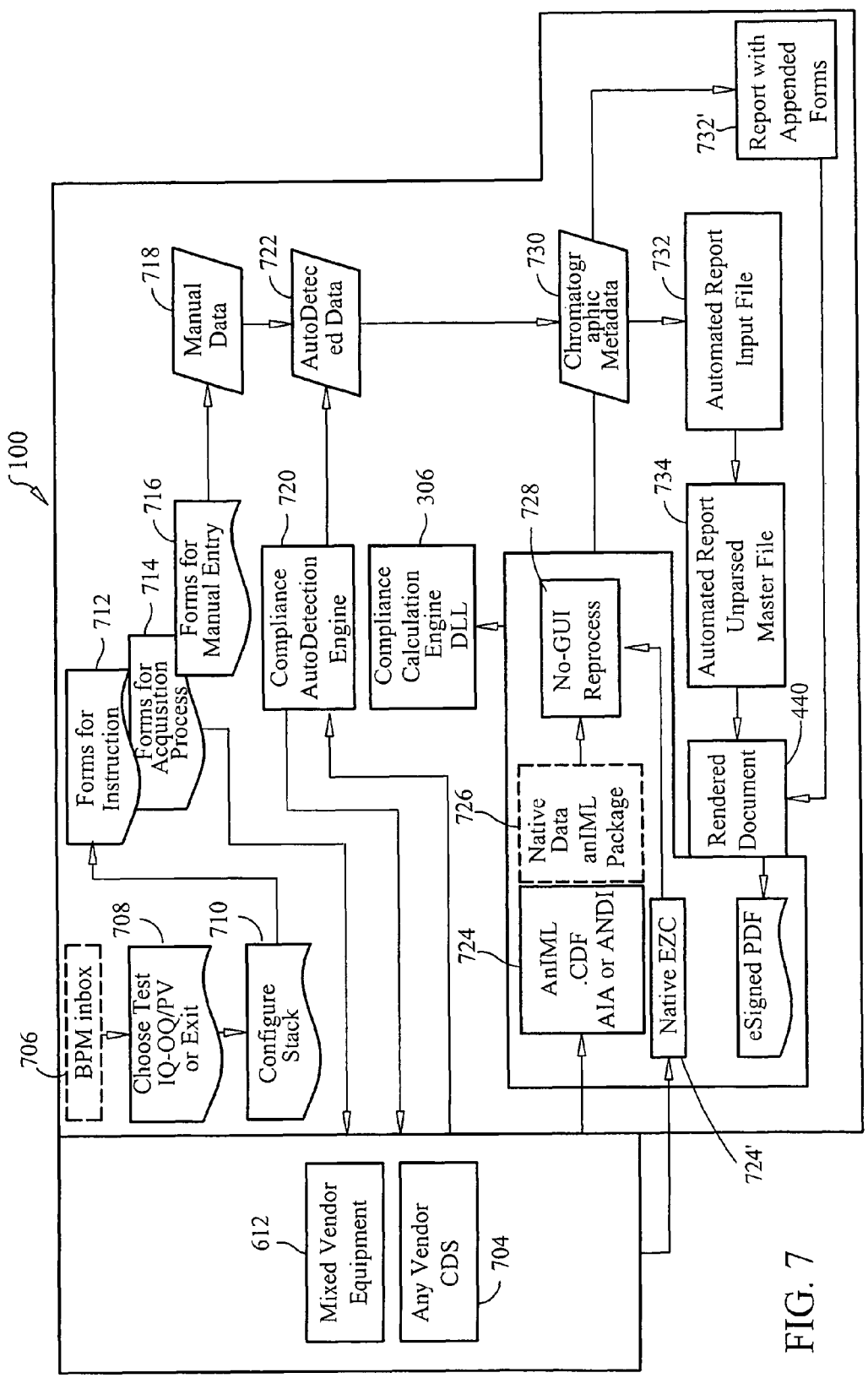
FIG. 7 is a schematic representation of an embodiment of a system for use in creating a compliance report for chromatographic instrumentation.

Referring now to FIG. 7, a schematic representation of an embodiment of system 100 is shown for use in creating a compliance report for chromatographic instrumentation. System 100 is represented as interfacing with native CDS to receive data inputs. In this example, the equipment being reported on is mixed vendor equipment 612, in which case, any or all of the vendor's computer data systems 704 may be employed through which data is inputted to system 100. Typically, however, a common data system controller (CDS) is provided to control all of the mixed vendor modules, as noted above. Forms 200 (which may optionally be driven by BPM 406, in which case forms 200 may be presented to a user by placement into a user-specific inbox, e.g., BPM Inbox 706, that functions similarly to the inbox of an e-mail service) are presented to a user of system 100 for forming a compliance report. For example, simple instructions can be provided in a "wizard" like environment (i.e., where simple tasks are completed sequentially and interactively). Thus, if a message is placed in inbox 706 that instructs a simple task to be performed, once the task is performed or "Done", then the next task can be emailed or placed into inbox 706. At event 708, whether or not BPM 406 is employed, a user, or manager assigning tasks to a user, may choose the type of test or qualification to be performed. In response to this choice system 100 may then run a template to call the correct forms to be completed for the chosen test. Configure stack 710 provides a configuration-specific template which determines the required tests, forms and instructions to be processed. Forms for Instruction 712 are one option for processing, herein these forms 200 associated with a qualification event may contain simple instructions for processing with no data entry potential. Forms for Acquisition Process 714 provide another option for processing according to forms associated with a qualification event in which forms 200 may describe the setup of the native data system to perform specific runs and acquire specific data from the instrument and/or software to be qualified. Those same forms 200 may provide controls for entry (which may be manual and/or automated) of the results obtained from the processes run with respect to the native computer data system to obtain the specific data. Forms for Manual Entry 716 are forms 200 in which manual entry may be made directly to. Alternatively, entry may be made to these forms 200 via an application supplied user interface when required by a system being tested. Manual data 718 refers to a further embodiment of forms 200 that may be created such that form elements are present to allow manual, interactive entry of data from an attendant user. Forms 200 may also be constructed as a mixed model where some elements of the forms 200 are automatically filled in when the data is available to the system. When data is not available to the system for automatically filling in the forms 200, such data can be interactively filled in (manually) by a user.

Compliance auto detection engine 720 may be an applet very similar to calculation engine 306 that stores or accesses identifying characteristics regarding various types, manufacturers, etc. of equipment. So for example, where a form requests a model number and serial number of an instrument 612, rather than requiring a user to manually enter this information, autodetection engine 720 queries the software 704 associated with the piece of equipment 612 to obtain the required information and then automatically enters it into the form 200 from which the request originated. If autodetection engine 720 is unsuccessful in automatically retrieving some or all of the information that was queried for, system 100 leaves the entries for this information on the applicable forms 200 blank and presents the forms for manual completion in addition to the automatic generation (autodetected data 722) to whatever extent was possible.

Data storage and format conversion of the inputted data may be performed by system 100 (optionally, by ECM 404 as controlled by BPM 406) in accordance with the instructions contained in forms 200 selected for processing the data, wherein forms 200 identify the particular data that is needed. In this example, data may be converted to AnIML formatting 724 or other common data form (CDF), such as AIA (Analytical Instrument Association) or ANDI (Analytical Data Interchange) format (typically annotated with .CDF extensions). When converting to AnIML, Native Data AnIML package 726 may be employed to provide/store the data in the AnIML format as well as in the native CDS format. Analog data from an instrument may be A/D converted into a standardized format 724' for use by the system 100, such as AIA or Native EZC format or other compatible input format to reduction engine 302, for example.

In any case, once the data is converted, data reduction engine 302, (whether integrated to ECM 404 or standalone) may perform reprocessing of the data in accordance with the needs of the final report to be generated, as instructed by the forms 200 that need to be filled out (and which may optionally be guided by BPM 406, as noted above). Reprocessing/data reduction calculations can be can be driven by API, so that no user interface is required (i.e., No-GUI Reprocess 728). Thus, data can be inputted directly from an instrument's operating software 704 to instrument 100 where it may be converted to a technology-neutral format and then fed directly to data reduction engine 302.

The reduced/reprocessed data is forwarded to calculation engine 306 (in this example, calculations are performed for a compliance report, and engine 306 is referred to as a compliance engine) for further calculations that are instructed by forms 200. Calculation engine 306 may mine forms 200 that have been populated by the reprocessing by data reduction engine 302, or may obtain data from mining results based on matching names to name-value pairs as described above, perform the instructed calculations, and, together with the reprocessed data, output metadata 730, which is chromatographic metadata in this example. This processing may also be API driven, so that all processing may be carried out in the background, without interrupting a user for interactive input.

However, even if all the automation cannot work as intended, (such as when an instrument lacks adequate software or other capability for automatically interacting with system 100, for example) then system 100 may launch user interface 250 to accept some interactive input from a user, under guidance of a standard operating procedure, so that the user can interactively choose information to be filled in. Even the calculation engine 306 is designed to work as an API, as noted. However, a user interface 250 may also be provided for calculation engine 306 to allow a user to use it as a custom calculator, for example, so that the same results can be manually calculated, through interface with a user, since the custom calculator uses the same engine 306 that the automated client uses.

Any or all of the manual data 718, autodetected data 722 and metadata 730 may require some additional manual entry(ies) depending upon the particular instrument from which data is being obtained. Examples of metadata entries that may need to be entered manually include, but are not limited to results of data collected from a source other than the data source provided by the native CDS, such as readings from onboard sensors, readings from external measurement devices, etc. Forms 200 that contain the manual data 718, autodetected data 722 and metadata 730 are mined for the specific data required by the final report 444 to be created (such as by using record mining engine 440), and the mined data may be forwarded to an automated report generator application 442 that assembles the mined data into an automated report input file 732 which is forwarded to an unparsed master file 734, from which the automated report application renders the final document 440.

Alternatively, an automated report application need not be implemented. For example, final reports 732' may be embodied by completed forms 200 without the need to data mine such forms. Further alternatively, a final report may be compiled by mined data that is simply assembled and attached to the forms 200 containing metadata. Everything between the raw data (e.g., original data received from an instrument or instrumentation software) and the final reported values is considered metadata. Metadata may be raw data or mined data or a combination thereof as it is used to populate a form. Some pre-final data may already be provided on a form while additional pre-final data may need to be added by the process. The data on the forms 200 can all be considered metadata in the sense that it is used to create the final report data so it qualifies as data about the final report data.

In instances wherein BPM 406 is employed, BPM 406 may then forward the final document, such as via e-mail, for example, to have the final document (which may be in pdf format, as in the example shown in FIG. 7) signed. Alternatively, the final document may be manually forwarded by a user, such as by the user emailing or otherwise forwarding the final document. The final report cannot be modified by those reviewing it, but must be reprocessed by the system 100 if changes are to be made. The process flow for such a rerun or re-evaluation involves returning the process to the step that begins processing the information that is desired to be re-evaluated. However, if this is not done, then any changes will still be captured by system 100 (or by ECM 404, if used) through its automatic audit trails functionality. Further, BPM 406, together with ECM 404 may track the review process and store records of the same to maintain the chain of the audit trail. The final report 440 is thus a defensible piece for use in meeting compliance regulations.

Forms 200 provide the basis for processing data by system 100. Wizard-like central data collection may be provided wherein either the automated client or a user are provided with simple tasks to complete by filling in the appropriate data, which may require a user to type in, scan in, select, or otherwise enter data, or which may require the automated client to query the instrument's software for the data which is then inputted to the form, or to perform calculations on select technology neutral data having been converted from the native data received from the software of the instrument, or other processing as instructed by the particular task presented by the form. In their most basic configuration, forms 200 are provided to generate a customer deliverable, typically a final report containing specifically requested or required data. Thus, forms 200 with standard defaults may be provided to automatically generate such a final report.

Further, forms 200 stored in ECM 404 may be configured to function to provide an audit trail (such as by storing versions of the forms as they are completed, together with data and time stamp, for example). Further, forms 200 may be configured to contain instructions for all processing by system 100. For example, certain forms 200 may contain specific instructions for calculations to be performed by calculation engine 306. Thus, forms 200 can be interactively filled out by a user through user interface 250, and/or can be programmatically filled out by autodetection processes or calculation engines.

Various combinations of forms 200, automation and custom reporting may constitute a final report by system 100. For example, forms 200 alone may be interactively filled out by a user to prepare a final report. Using ECM 404 together with forms 200, forms 200 along with the final report 444 may be centrally stored and provide an audit trail for support of the final product. By adding the automated calculation engines, such as data reduction engine 302, calculation engine 306 and records mining engine 440, for example, processing may be fully automated to provide a final report, if only according to a defaulted form of the final report 444. Adding the autodoumentation application 442 provides further flexibility, whereby a final report 444 can be customized. Note also, that the modules need not be combined as described, or in the order as described. For example, forms 200 may be combined only with automated report application 442, so that a final report 444 generated from manual inputs to forms 200 may be customized using the automated report application 442.

Further, a hierarchy of forms 200 may be provided for more efficient completion of forms 200 during processing. For example, a master form may be set up to feed other process forms. A master form generally contains information that is globally the same with respect to all process forms that it feeds. Accordingly, this permits global information to be filled out only once, after which is automatically appears in all of the subordinate forms 200 fed by that master form 200. Different types of master forms 200 may also be created. For example, a qualification master form 200 may contain global information such as customer information (address, names, etc.), instruments that a qualification will be covering, and/or acceptance limits for instrument categories. An instrument configuration master form 200 may contain a named configuration mapped to configuration details (e.g., a stack of instruments 612) and/or override limits for specific equipment needs. A stack, for example, may include all of one type of instrument, different vendors' instruments, or any combination of instruments, as the complexity of the stack can be programmed into an instrument configuration master form 200. Instrument configuration master forms 200 may be limited to only those instruments and vendors that are configuration master approved, to prevent a user from arbitrarily attempting to add an instrument to an instrument configuration master form for which there is no procedure for processing.

Using the methods and systems described herein, non-vendor specific instrument qualifications may be processed using a native controlling software of an instrument combined with a technology-neutral, standardized, post-collection data reduction and reporting model. Such processes may be provided by universally applicable, scalable, automated, secure and consistent platform for the development, and delivery of instrument qualification. Original data collected for the qualification may be accomplished using the native controlling software without the need to go through external analog to digital conversion or other manipulation. However, the system 100 is not precluded from using alternative data input methods, including, but not limited to data that has already been digitized; manual input of data, etc., as already noted above. Original data may be preserved for possible reanalysis by the native controlling software, and may also be converted to an accepted technology-neutral format allowing the data to be submitted to a single reprocess and calculation engine for consistent reduction and processing. Instructions may be instantiated as forms, which may provide procedural information as well as act as data repositories. Forms may be presented according to need and apply only to the instrument under test to reduce delivery complexity and error while providing audit trails for tracking.

Figure 8:
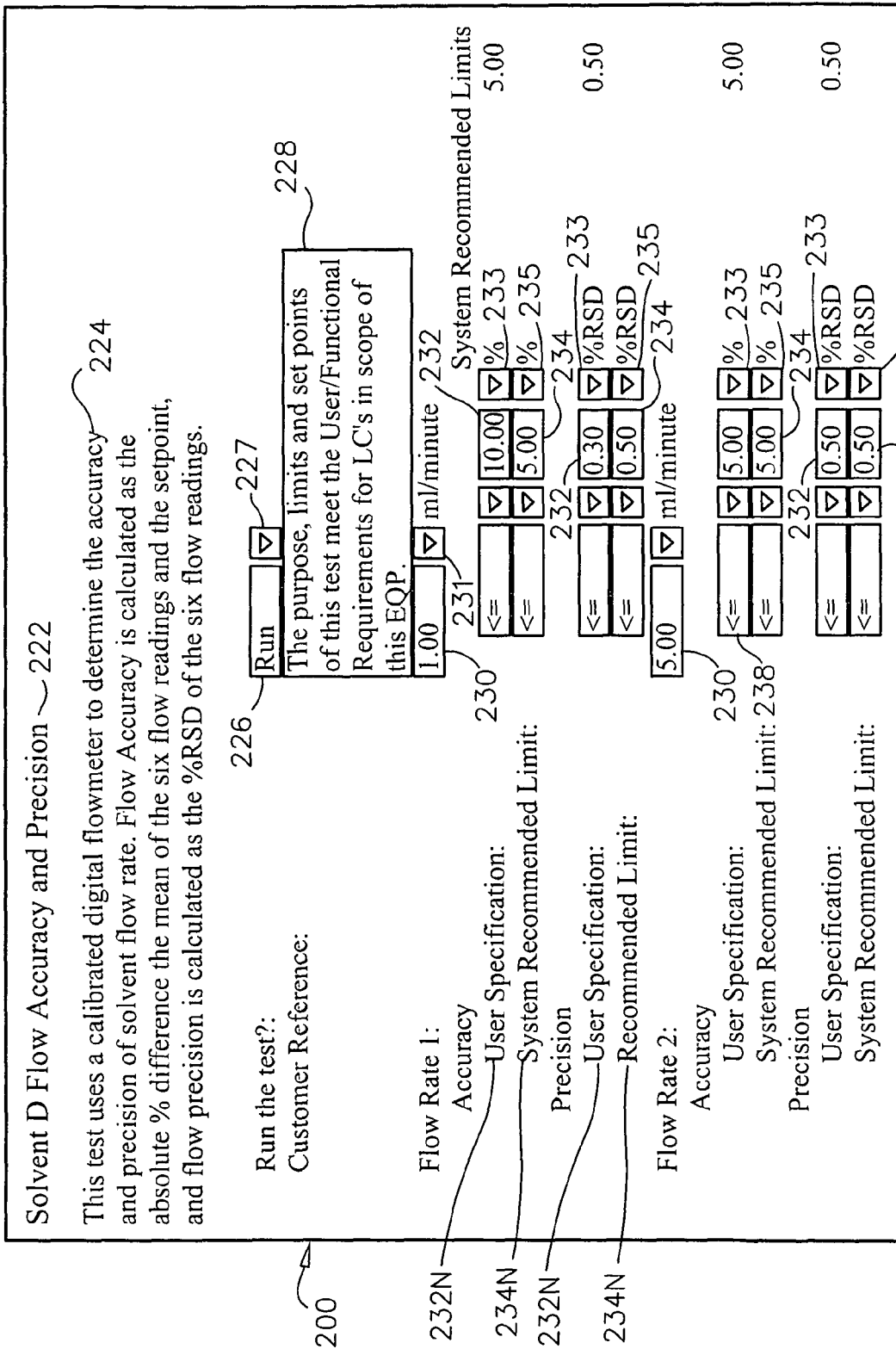
FIG. 8 illustrates another example of a form used in performing a test and qualifying test results against dual test limits.

FIG. 8 shows an example of a form 200 that may be provided for qualifying equipment, and may be used for recording test specification and report definitions in making qualification protocols. Each protocol may contain tests, with set points and limits, required to be executed on any single instrument or named group of equipment. Although FIG. 8 shows an example of a form 200 for testing flow accuracy and precision of solvent flow rate in a liquid chromatography apparatus, other tests/forms that may be included in a qualification protocol for such a liquid chromatography apparatus include, but are not limited to: accuracy and stability of column temperature; wavelength accuracy; signal noise and drift; injection precision and carry over; response linearity; solvent gradient composition accuracy, stability and linearity; and sample temperature accuracy. Of course, qualification by the present system 100 and forms 200 are not limited to liquid chromatography apparatus, but may be applied to other instrumentation, softwares and hardwares, as indicated above. A default list of tests, set points and limits may be provided for each type of qualification and instrument that may be qualified by the system 100, using recommended tests. The default set of tests may be accepted by a user, or a user-selected set of tests, optionally with user selected settings can be used for a custom configured qualification procedure.

While FIG. 8 is described with reference to a flow accuracy and precision test, it is noted that common features that apply to forms 200 for other quality tests are described here. The test name 222 is typically provided by the system, although, for custom-designed tests, form 200 may allow editing of the test name 222. A brief test description 224 may also be provided. Field 226 may be manipulated by the user to run the identified test (i.e., "Run", as shown), or to omit running this test, by toggling the field to "Don't Run", for example by selecting button 227 to visualize a drop down menu from which to select either "Run" or "Don't Run". The customer reference field 228 allows the user to input a description tailored to the user's needs for easily identifying/describing the test that is being performed, wherein specific equipment tested may also be identified. Test settings 230 (such as flow rates, for this example) are typically preset by the system, but may be modified by a user for customized testing, and many other purposes, such as by selecting from a drop down menu of available settings when selection on button 231.

Figure 9:
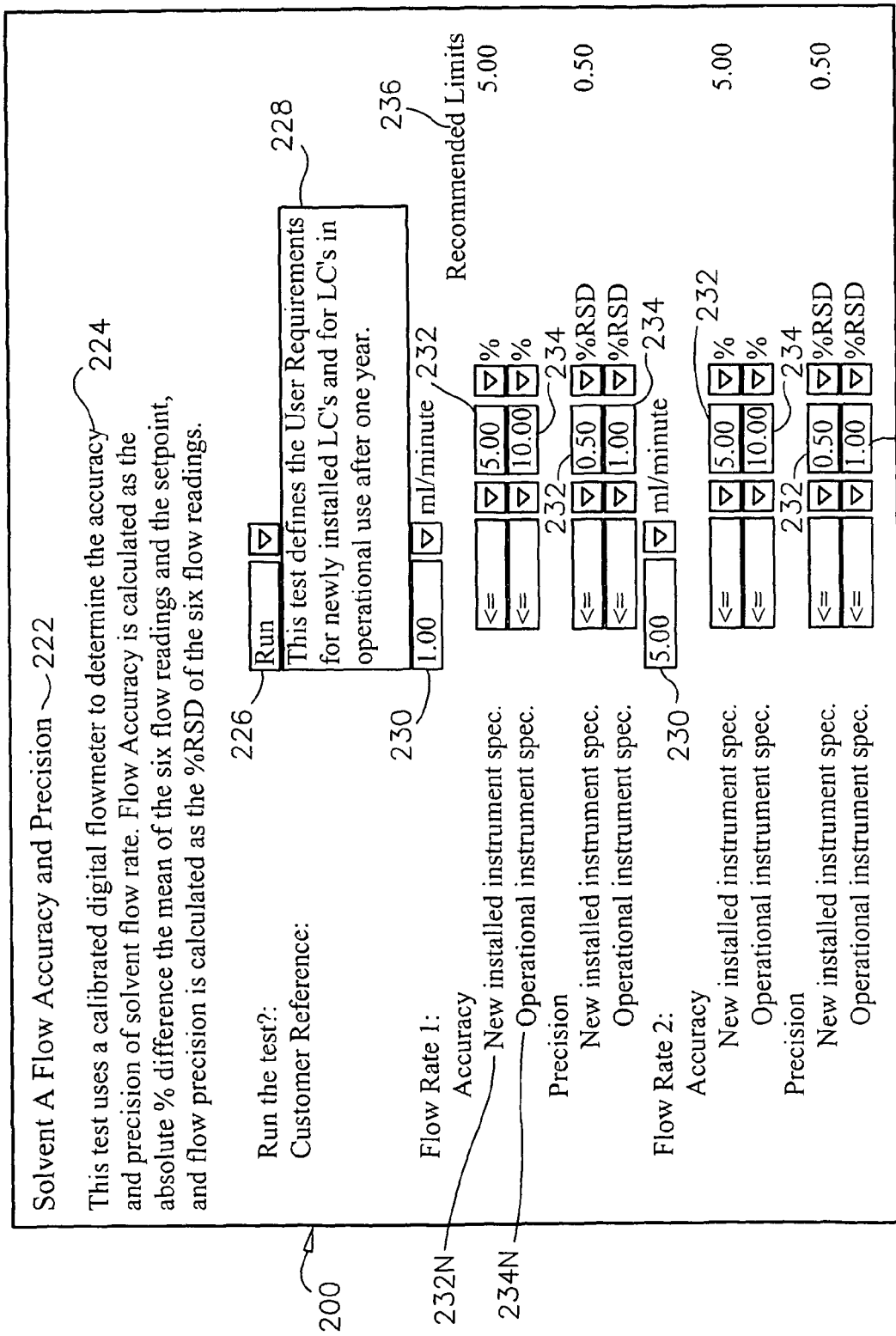
FIG. 9 illustrates another example of a form used in performing a test and qualifying test results against dual test limits.

FIG. 9 shows another example of a form 200 that may be provided for qualifying equipment, and may be used for recording test specification and report definitions in making qualification protocols, in which dual limit features are used for qualifying instruments according to their age or number of hours of use. In this example, the limits fro newly installed instruments have been chosen by the user to match the limits recommended 236 by the system/form 200, while a secondary set of limits 234 in this example have been chosen to be less stringent than the first set of limits 232 and are to be used for instruments that have been in operation for a year or more and for which it is generally accepted that a less stringent performance limit can be applied to account for normal wear and tear and mechanical degradation. Regardless of what the first 232 and second 234 limits are chosen to be by a user, the system recommended limits 236 are always provided in forms 200. For example, the recommended limits 236 provided may be provided as specifications typically found to meet international industry standards and regulatory expectations, in the judgment of the protocol developers.

Dual test limits (i.e., a more stringent limit and a less stringent limit) may be provided for any or all tests performed. The forms 200 may have system recommended limits preset in both sets of limits, which are then modifiable by a user, as noted in the example of FIG. 9 above. In the example shown in FIG. 8, the user has maintained the system preset limits in limit set 234 and limits 232 have been modified to less stringent limits. The user specification second limit 232 for Flow Rate 1: Accuracy has been changed to a less stringent limit (i.e., $\geqq 10.00\%$) than the corresponding limit 234, which in this case is left at the system recommended limit (i.e., $\geqq 5.00\%$). The user may modify a limit by selecting the button 233 (or 235) corresponding to the limit to be modified, and selecting a value from a resulting drop down menu of values. Thus, a user may individually modify any single limit 232 or 234 to a value that is less stringent or more stringent than the corresponding limit 234 or 232 in that dual limit set for a particular test. In the example of FIG. 8, the user has set the user specification limits 232 for accuracy and precision to be less stringent and more stringent, respectively, than the recommended limits, with regard to Flow Rate 1. For Flow Rate 2, the user specified limits 2322 have been left equal to the recommended limits 234. The names 232N and 234N for each respective limit may also be user modifiable, to name the limits appropriately, as can be noted in the names that have been entered by the user in the example of FIG. 9. For example, terminology naming the limits (i.e., names 232N and 234N) can be modified by the user to match the corporate glossary, procedural requirement, or department preferences or practices. The operator fields 238 for the limits may also be user modifiable. For example, the user may select button 239 and select a "$\leqq$" operator or a "$\geqq$" operator.

As another example of the use of dual limits, the user may want to make limits 232 more stringent than limit 234, so that if the instrument passes limit 234, but fails limit 232, the user is identified as such and knows that the instrument, in this case, passes the qualification, but may not meet internal standards. Or this may alert the user that the instrument, although currently passing, should be tested more frequently, as it may need recalibration and/or repair soon, since it failed the more stringent limit.

In other instances, a user may want to set user limits 232 less stringently than the recommended limits 234, depending upon the user's needs. Thus, for example, if something less stringent than the system's recommended limit is still a useful or useable limit for the user's intended purpose, then the user may set limit 232 to be less stringent than recommended limit 234. Upon running a dual limit test, the resulting status of the equipment tested is outputted. Default status names provided by the system include "Pass", "Pass recommended limit only", and "Fail", where "Pass" indicates the test result meets both of the set limits 232 and 234, "Pass recommended limit only" indicates that the test result mess the less stringent limit, but not the more stringent limit, and "Fail" indicates that the test result does not meet either limit. These status names may also be user-modifiable to any name or term desired.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular hardware, software, instrument, module, process, process step or steps, to the objective, spirit and scope of the present invention. All such modifications are intended to be within the scope of the claims appended hereto.

The invention claimed is:

1. A computer-implemented method of compliance testing, said method comprising:
   inputting data from at least one analytical instrument or controlling software of an analytical instrument to a system;
   converting said inputted data of said at least one analytical instrument or said controlling software to a technology-neutral format;
   performing one or more calculations on said inputted data, using a computer-implemented analytical instrument compliance system, to produce one or more outputs;
   selecting from said one or more outputs to populate a final report; wherein said one or more outputs are standardized and are directly comparable to outputs resultant from said method carried out on another set of one or more other analytical instruments or controlling softwares for analytical instruments, irrespective of manufacturer or model of said other analytical instruments;
   comparing at least one of said outputs to first and second test limits indicative of said instrument's performance; and
   reporting compliance status of said at least one output based on said comparing to said first test limit and to said second test limit.

2. The method of claim 1, wherein said data is converted to said technology neutral format prior to said inputting.

3. The method of claim 1, wherein said data is converted to said technology neutral format after said inputting.

4. The method of claim 1, wherein at least one of said first and second test limits is user-settable.

5. The method of claim 1, wherein one of said first and second test limits is automatically preset.

6. The method of claim 1, wherein said performing one or more calculations comprises data reduction, said data reduction being carried out by a data reduction engine, wherein the same data reduction engine may be used for data received from multiple analytical instruments.

7. The method of claim 6, further comprising inputting results of said data reduction to a calculation engine and performing at least one further calculation based upon said inputted results.

8. The method of claim 1, wherein said calculations are performed to answer a series of questions relating to one or more performance tests designed to determine compliance of said analytical instrument or software under consideration with a set of predefined criteria.

9. A computer-implemented method of compliance testing, said method comprising:
   inputting data from at least one analytical instrument or controlling software of an analytical instrument to a system;
   performing one or more calculations on the inputted data, using a computer-implemented analytical instrument compliance system, to produce one or more outputs;
   selecting from said one or more outputs to populate a final report; wherein the one or more outputs are standardized and are directly comparable to outputs resultant from said method carried out on another set of one or more other analytical instruments or controlling software for analytical instruments, irrespective of manufacturer or model of the other analytical instruments;
   comparing at least one of said outputs to first and second test limits; and
   reporting compliance status of said at least one output based on said comparing to said first test limit and to said second test limit;
   wherein said performing one or more calculations are performed according to instructions instantiated as forms.

10. The method of claim 9, wherein said forms contain data generated from at least one of interactive manual input, information detected by a system performing said method, a computerized data system of an instrument from which data is being converted, and calculated, reduced data.

11. The method of claim 9, wherein said forms include launch points for executables that perform functions performed by said method.

12. The method of claim 9, further comprising storing said outputs of performed calculations on the forms.

13. The method of claim 9, further comprising storing said forms in a database as a repository of processed data.

14. The method of claim 13, further comprising identifying an audit trail based upon forms and data stored in the database.

15. A computer-implemented method of compliance testing, said method comprising:
   inputting data from at least one analytical instrument or controlling software of an analytical instrument to a system;
   performing one or more calculations on said inputted data, using a computer-implemented analytical instrument compliance system, to produce one or more outputs;
   selecting from said one or more outputs to populate a final report; wherein said one or more outputs are standardized and are directly comparable to outputs resultant from said method carried out on another set of one or more other analytical instruments or controlling softwares for analytical instruments, irrespective of manufacturer or model of said other analytical instruments;
   comparing at least one of said outputs to first and second test limits indicative of said instrument's performance, wherein said comparing is performed according to instructions instantiated as forms; and
   reporting compliance status of said at least one output relative to based on said comparing to said first test limit and to said second test limit.

16. The method of claim 15, wherein at least one of said forms contains said first and second test limits.

17. The method of claim 16, wherein at least one of said first and second test limits is user-specifiable.

18. A computer-implemented method of compliance testing, said method comprising:
   inputting data from at least one analytical instrument;
   converting said inputted data to a technology-neutral format if said inputted data is not already in said technology-neutral format;
   performing one or more calculations on said inputted data in said technology-neutral format, using a computer-implemented analytical instrument compliance system, to produce one or more outputs;
   comparing at least one of said outputs to first and second test limits indicative of said instrument's performance; and
   reporting compliance status of said at least one output based on said comparing to said first test limit and to said second test limit.

19. A method of compliance testing at least one of analytical instrumentation and analytical instrumentation software, said method comprising:
   displaying a test protocol form configured for said compliance testing of said at least one of analytical instrumentation and analytical software on a user interface and prompting a user to input information regarding a test for qualifying a result of the test;
   prompting at least one analytical instrument or analytical instrument software associated with an analytical instrument to initiate the test protocol, either in response to an input by the user into the test protocol displayed on the user interface, or in response to results from another analytical instrument in response to a test protocol run on the another analytical instrument;
   automatically calculating results of the test protocol run on the at least one analytical instrument; and
   outputting status of the results as determined by comparing said results to at least one set of dual test limits.

20. The method of claim 19, further comprising inputting a first test limit value, by a user, of at least one of said at least one set of dual test limits.

21. The method of claim 20, wherein a second test limit value of said at least one set of dual test limits in which said first test limit was user inputted, is automatically preset.

22. The method of claim 21, wherein said first test limit is more stringent than said second test limit.

23. The method of claim 19, further comprising selecting from said one or more outputs to populate a final report; wherein said one or more outputs are standardized and are directly comparable to outputs resultant from said method carried out on another set of one or more other instruments and/or software, irrespective of manufacturer or model of the other analytical instruments.

24. A system for standardizing characterizations of at least one of analytical hardware and controlling software during compliance testing, said system comprising:
   a data reduction engine configured to reduce data outputted by an analytical instrument;
   a calculation engine configured to perform at least one calculation on at least one of said data outputted by an analytical instrument and the reduced data to produce one or more outputs required for a set of predefined criteria; and interactive forms comprising computer executable format executable by said system to provide instructions executable by said data reduction engine and said calculation engine, said forms providing procedural information including calculation instructions;

wherein said interactive forms provide instructions for calculating outputs to answer one or more questions relating to one or more performance tests designed to determine compliance of the at least one of analytical instrument and controlling software.

25. The system of claim 24, wherein said data reduction engine reduces said data to a technology-independent, reduced metadata set.

26. The system of claim 24, wherein at least one of said interactive forms includes dual test limits.

27. The system of claim 24, further comprising algorithms for converting data from a native format as outputted by an analytical instrument to a technology-neutral format.

28. The system of claim 24, further comprising an automatic detection engine configured to determine at least one of instrument and controlling software specific information to automatically characterize said at least one of said instrument and said controlling software.

29. The system of claim 24, wherein said outputs are stored on said forms.

30. The system of claim 29, further comprising means for mining said forms to extract metadata needed to produce a final report.

31. The system of claim 30, further comprising means for compiling the extracted metadata into the final report.

32. The system of claim 24, further comprising a user interface configured to facilitate manual input to at least one of said interactive forms by a user.

33. A non-transitory computer readable medium carrying one or more sequences of instructions for compliance testing, wherein execution of said one or more sequences of instructions by one or more processors causes said one or more processors to perform:

inputting data from at least one analytical instrument;

converting said inputted data to a technology-neutral format if said inputted data is not already in said technology-neutral format;

performing one or more calculations on said inputted data in said technology-neutral format to produce one or more outputs, comparing at least one of said outputs to first and second test limits indicative of said instrument's performance; and reporting compliance status of said at least one output based on said comparing to said first test limit and to said second test limit.

34. A computer-implemented method of compliance testing at least one of instrumentation and software, said method comprising the steps of:

inputting data from said at least one analytical instrument or software to a computer-implemented analytical instrument compliance system;

performing one or more calculations on the inputted data, using the computer-implemented analytical instrument compliance system, to produce one or more outputs;

comparing at least one of said outputs to first and second test limits, wherein said comparing is performed according to instructions instantiated as forms;

selecting from said one or more outputs to populate a final report and reporting compliance status of said at least one output based on said comparing to said first test limit and to said second test limit;

wherein the at least one output is standardized and are directly comparable to outputs resultant from said method carried out on another set of one or more other analytical instruments, irrespective of manufacturer or model of the other analytical instruments.

35. A system for standardizing characterizations of at least one of analytical hardware and controlling software during compliance testing, said system comprising:

a data reduction engine configured to reduce data outputted by an instrument;

a calculation engine configured to perform at least one calculation on at least one of said reduced data to produce one or more outputs required for a set of predefined criteria;

an automatic detection engine configured to determine at least one of instrument specific information to automatically characterize said instrument; and interactive forms comprising computer executable format that provides instructions executable by said data reduction engine, said calculation engine and said automatic detection engine, said forms providing procedural information including calculation instructions.

36. A computer-implemented method of compliance testing, said method comprising:

inputting data from at least one analytical instrument or controlling software of an analytical instrument to a computer-implemented analytical instrument compliance system;

converting said inputted data to a technology-neutral format if said inputted data is not already in said technology-neutral format;

performing one or more calculations on said inputted data in said technology-neutral format, using said computer-implemented analytical instrument compliance system, to produce one or more outputs; and selecting from said one or more outputs to populate a final report; wherein said one or more outputs are standardized and are directly comparable to outputs resultant from said method carried out on another set of one or more other analytical instruments or controlling softwares for analytical instruments, irrespective of manufacturer or model of said other analytical instruments, wherein said calculations are performed to answer a series of questions relating to one or more performance tests designed to determine compliance of said analytical instrument or software under consideration with a set of predefined criteria indicative of said instrument's performance.

37. A computer-implemented method of compliance testing, said method comprising:

inputting data from at least one analytical instrument or controlling software of an analytical instrument to a system;

performing one or more calculations on the inputted data to produce one or more outputs;

selecting from said one or more outputs to populate a final report; wherein the one or more outputs are standardized and are directly comparable to outputs resultant from said method carried out on another set of one or more other analytical instruments or controlling softwares for analytical instruments, irrespective of manufacturer or model of the other analytical instruments;

comparing at least one of said outputs to first and second test limits; and reporting compliance status of said at least one output based on said comparing to said first test limit and to said second test limit;

wherein said performing one or more calculations are performed according to instructions instantiated as forms; and wherein said forms contain data generated from at least one of interactive manual input, information detected by a system performing said method and software of system, a computerized data system of an instrument from which data is being converted, and calculated, reduced data.

* * * * *

UNITED STATES PATENT AND TRADEMARK OFFICE
CERTIFICATE OF CORRECTION

PATENT NO. : 7,890,285 B2  Page 1 of 1
APPLICATION NO. : 11/286198
DATED : February 15, 2011
INVENTOR(S) : Charles Manfredi It is certified that error appears in the above-identified patent and that said Letters Patent is hereby corrected as shown below:

In column 20, line 2, in Claim 15, after "output" delete "relative to".

Signed and Sealed this
Nineteenth Day of April, 2011

David J. Kappos
*Director of the United States Patent and Trademark Office*